United States Patent [19]

Gouveia

[11] 4,181,233
[45] Jan. 1, 1980

[54] ONE-WAY VALVE STOPPER
[75] Inventor: Philip H. Gouveia, Metuchen, N.J.
[73] Assignee: Becton, Dickinson and Company, Rutherford, N.J.
[21] Appl. No.: 960,935
[22] Filed: Nov. 15, 1978
[51] Int. Cl.² .............................................. B65D 47/36
[52] U.S. Cl. .................................... 215/247; 215/260
[58] Field of Search ................ 215/247, 248, 249, 260

[56] References Cited
U.S. PATENT DOCUMENTS

| | | | |
|---|---|---|---|
| 2,153,981 | 4/1939 | Heineman | 215/248 |
| 3,136,440 | 6/1964 | Krug | 215/247 |
| 3,913,781 | 10/1975 | Andreux | 215/260 X |

FOREIGN PATENT DOCUMENTS 542956 3/1956 Italy ...................................... 215/260

*Primary Examiner*—Donald F. Norton
*Attorney, Agent, or Firm*—Kane, Dalsimer, Kane, Sullivan and Kurucz

[57] ABSTRACT

A one-way valve located anywhere on a stopper used in vacuum blood collection tubes, which permits venting or displacing any positive air pressure in a filled vacuum tube so that, when the pressure of the filled tube is greater than the pressure of the vein, the valve is actuated in the open position and when the pressures equalize, the valve closes. Such device also provides other advantages hereinafter set forth.

4 Claims, 6 Drawing Figures

ONE-WAY VALVE STOPPER

BACKGROUND OF THE INVENTION

1. Field of the Invention

The invention relates to stoppers for vacuum blood collection tubes and more particularly to a one-way valve stopper.

2. Brief Description of the Prior Art

U.S. Pat. No. 3,831,629 (Mackal et al) discloses a two piece check valve with a valve body and a valve element having an elastomeric rear end portion which is held in axial compression to constantly urge the valve element forwardly toward valve-closed position. The specification states that it is well suited for use in applications in which it is subjected to low-fluid pressures, i.e., a catheter. It mentions no use in a stopper for a blood collection tube. It is doubtful that it would be suitable or desirable for that purpose.

U.S. Pat. No. 3,943,969 (Rubin et al) discloses a check valve with spring means to effectively block fluid flow. The spring means normally urges the valve to a closed position and is adapted to open in response to a predetermined upstream line pressure. It mentions possible use in an irrigation system. It does not propose use for a stopper in a blood collection tube. Because of its involved construction it probably would not be desirable for use for that purpose.

SUMMARY OF THE INVENTION

The invention comprises a one-way valve stopper for sealing a vacuum blood collection tube, which comprises:

a passageway extending through the stopper from the inside of the tube to the outside of the stopper;

a valve interposed in the passageway to open and close the passageway depending on the pressure in the tube;

the said valve comprising:

a piston;

a plug at the end of the piston to close the passageway;

a vent from the valve to evacuate pressure when the plug is open; and a compression spring extending around the piston to keep the plug in a normally closed position;

the compression of the spring being determined according to the differentials between the pressure in the vein and the pressure in the tube.

DETAILED DESCRIPTION OF THE PREFERRED EMBODIMENTS OF THE INVENTION

Figure 1:
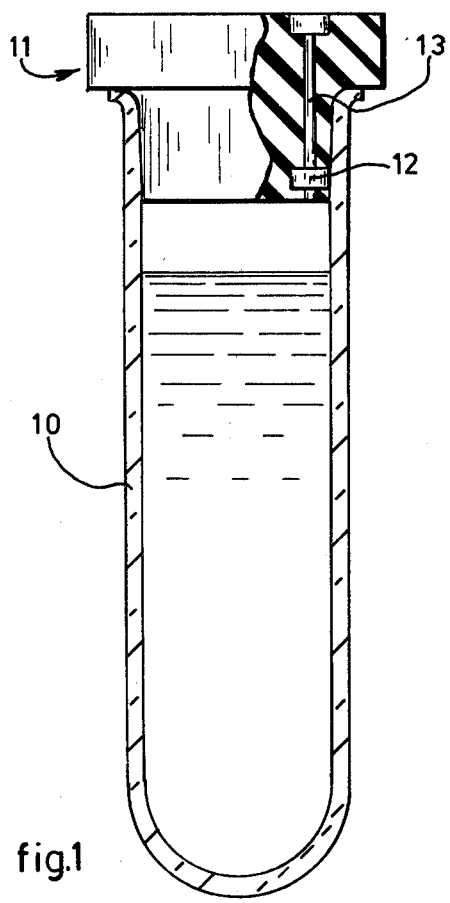
FIG. 1 is a side elevation, partly in section, of a vacuum blood collection tube with a stopper embodying a one-way valve.
Figure 2:
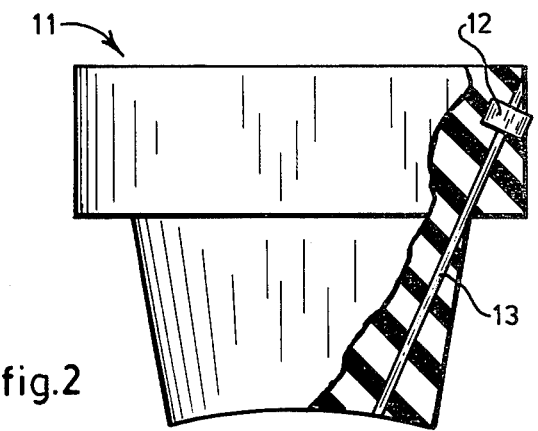
FIG. 2 is an enlarged view of a stopper for the vacuum blood collection tube of FIG. 1 with the valve in a different position in the stopper.

Referring to the drawings there is shown in FIG. 1 a conventional vacuum blood collection tube 10 which is sealed with a stopper 11. Embodied in the stopper is a one-way valve 12 which is interposed in a passageway 13 extending from a surface of the stopper inside of the tube to a surface of the stopper which is outside of the tube. Such passageway permits, subject to the valve, pressure in the tube to be vented. FIG. 2 shows a stopper similar to that of FIG. 1 but with the passageway and valve in a different position in the stopper. Such passageway and valve can be located anywhere in the stopper as long as it permits the pressure to be vented from the tube. The only restriction is that the passageway and valve not be located along the injection site of the needle through the stopper. Although the valve is shown at the inner end of the passageway in FIG. 1, it can also be positioned at the outer end of the passageway as shown in FIG. 2.

The valve 12 (FIGS. 3 and 4) comprises a piston 14 at the end of which is a plug 15 adapted to close the bottom opening 16 of the valve. A compression spring 19 surrounds the piston and presses downward against the outer periphery of the plug 15. The spring 19 is held at its upper end by a retaining ring 17 secured to the top of the valve chamber 18. There is clearance between the retaining ring 17 and the piston to permit pressure to be vented through the valve into the passageway 13. The valve shown in FIG. 5 is similar to that of FIGS. 3 and 4 except that the plug, instead of being flat at its bottom face, is tapered to fit into the opening 16 at the bottom of the valve.

Figure 3:
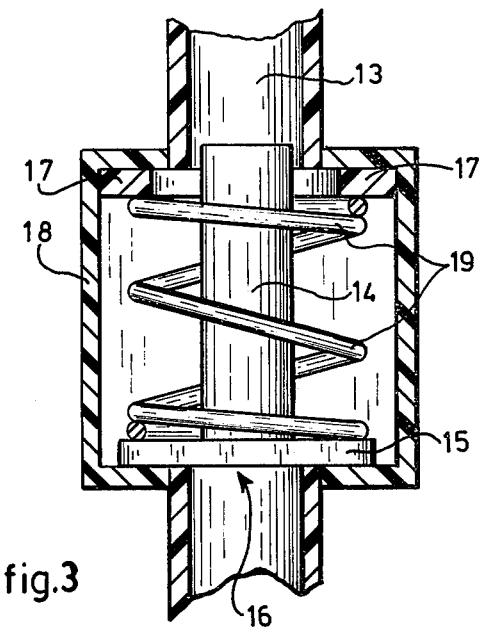
FIG. 3 is a sectional view of the one-way valve with the valve in the closed position.
Figure 4:
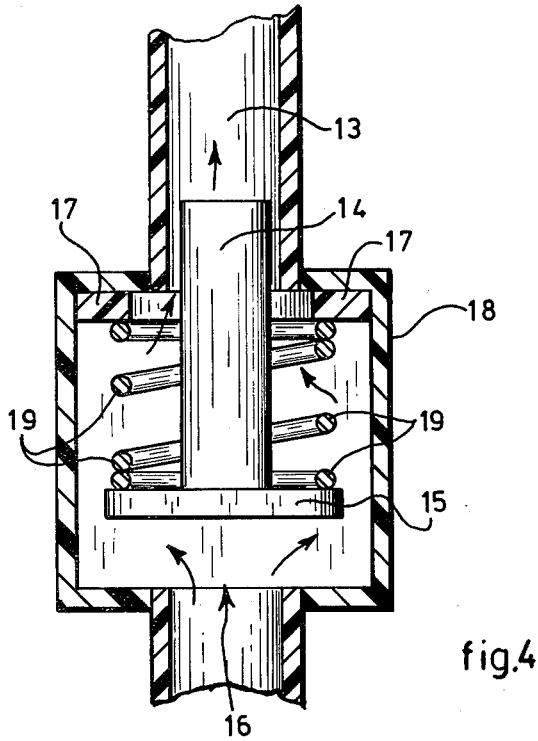
FIG. 4 is a sectional view of the valve of FIG. 3 with the valve in the open position.
Figure 5:
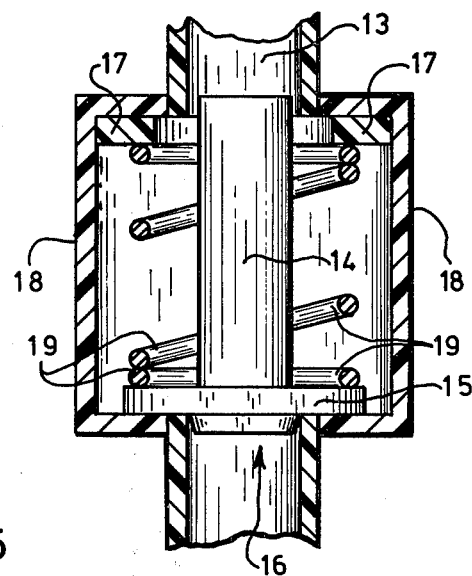
FIG. 5 is a sectional view of a one-way valve similar to that of FIG. 3 with a tapered plug.

The valves shown in FIGS. 3 and 5 provides means for venting or displacing any positive air pressure in a filled vacuum blood collection tube, thus relieving any back flow problem and allowing for use of the tube in any position.

Figure 6:
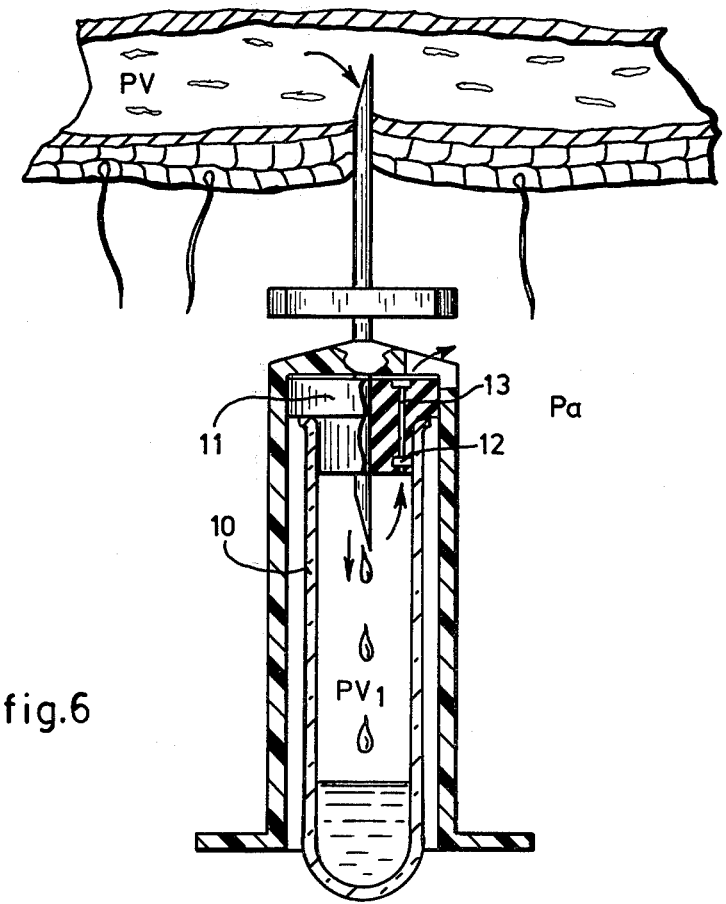
FIG. 6 is a sectional view showing a vacuum blood collection tube, a stopper embodying the one-way valve and a holder for the tube, with the needle inserted into a vein.

FIG. 6 illustrates the use of the valve in drawing blood from a vein. The vacuum blood collection tube sealed with the one-way valve stopper is held in a conventional holder with one end of the needle inserted in the vein and the other end of the needle inserted through the top of the stopper. It will be noted that the valve and passageway are located through the top of the stopper adjacent the point of injection of the needle through the stopper. As pointed out above the valve and passageway can be located anywhere in the stopper so long as it permits pressure to be vented from the tube and does not interfere with the injection site. The various pressures have been labeled as follows:

$Pv$ = Venial pressure $Pv_1$ = Tube pressure $P_a$ = Atmospheric pressure

When the tourniquet is released pressure $Pv$ momentarily increases. The valve actuates to the open position when the pressure $Pv_1$ in the tube exceeds the pressure $Pv$ in the vein. When pressure $Pv$ and $Pv_1$ equalize, the valve closes. While the blood sample is being taken the following pressure differentials occur to actuate the valve operation:

When $Pv > Pv_1$—valve stays closed until pressure $Pv_1 > Pv$.

When $Pv = Pv_1$—valve stays closed.

When $Pv < Pv_1$—valve stays open until $Pv = Pv_1$ and blood flow stops.

In addition to the primary purpose of the one-way valve stopper to displace or vent any positive pressure in a filled vacuum tube, as described above, such stopper also has the following advantages:

1. The use of such stopper eliminates the necessity of partially assembling the stopper and provides a better method of evacuating. This results in savings of production time. Once the stopper is fully assembled, the valve can be used to evacuate the tubes when put into an evacuation chamber. There will be no need to seat the stopper completely since it will be in that position to begin with.

2. By providing a valve in the stopper, a better seal can be obtained. The need for a vent slot can be eliminated.

3. With the use of a one-way valve and port in a stopper, the vacuum in the tubes can be checked by the use of an external gauge and monitoring devices.

Those skilled in the art will appreciate that many variations of the above described embodiment of the invention may be made without departing from the spirit and the scope of the invention.

What is claimed:

1. A one-way valve stopper for sealing a vacuum blood collection tube comprising:
   an injection area in the stopper through which a needle can be inserted for passing blood from a vein into the tube;
   a passageway extending through the stopper from the inside of the tube to the outside of the stopper, the said passageway being located in the stopper outside of the injection site;
   a valve interposed in the passageway to open and close the passageway;
   the said valve comprising:
      a housing enclosing the valve having top and bottom openings;
      a piston;
      a plug at the end of the piston adapted to close the bottom opening and passageway;
      a vent from the housing to evacuate pressure when the plug is open; and
      a compression spring extending around the piston to keep the plug in a normally closed position;
   the compression of the spring being determined according to the differentials between the pressure in the vein (Pv) and the pressure in the tube ($Pv_1$);
   whereby when $Pv_1$ is greater than Pv the valve is actuated to the open position and when $Pv_1$ is equal to or less than $P_v$ the valve will remain in the closed position.

2. The stopper of claim 1 in which the passageway extends from the top to the bottom of the stopper and is adjacent to the injection site.

3. The stopper of claim 1 in which the passageway extends diagonally from the side of the stopper above the top edge of the tube to the bottom of the stopper.

4. The stopper of claim 1 in which the plug of the valve is tapered to fit into the plug bottom opening of the housing.

* * * * *